United States Patent
Levorse, Jr. et al.

(10) Patent No.: US 7,329,637 B2
(45) Date of Patent: Feb. 12, 2008

(54) METHYLENE DIOXY OCTAHYDROINDENE DERIVATIVES

(75) Inventors: Anthony T. Levorse, Jr., Westfield, NJ (US); Brett D. Newirth, Atlantic Highlands, NJ (US); Manfred Pawlak, Princeton, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 649 days.

(21) Appl. No.: 11/021,068

(22) Filed: Dec. 23, 2004

(65) Prior Publication Data

US 2006/0142176 A1   Jun. 29, 2006

(51) Int. Cl.
*A61K 8/00* (2006.01)
(52) U.S. Cl. .......................... 512/12; 512/13; 549/359; 549/369
(58) Field of Classification Search ................. 512/12, 512/13; 549/359, 369
See application file for complete search history.

(56) References Cited

U.S. PATENT DOCUMENTS

| 4,211,674 | A | * | 7/1980 | Lenselink ...................... 512/9 |
| 6,303,798 | B1 | | 10/2001 | Belko et al. |
| 7,122,513 | B2 | * | 10/2006 | Levorse et al. ............... 512/25 |
| 7,176,324 | B1 | * | 2/2007 | Levorse et al. ............. 549/430 |

FOREIGN PATENT DOCUMENTS

GB     714 645 A     9/1954

OTHER PUBLICATIONS

A. Abate et al., Helvetica Chimica Acta vol. 86, issue 3, Feb. 2003.*
Brenna E. et al. "Enantioselective perception of chiral odorants", Tetrahedron: Asymmetry Report No. 54, Elsevier Science Publishers, Amsterdam, NL, vol. 14, No. 1, Jan. 6, 2003, pp. 1-42.

* cited by examiner

*Primary Examiner*—John R. Hardee
(74) *Attorney, Agent, or Firm*—Elizabeth M. Quirk; Joseph F. Leightner

(57) ABSTRACT

The present invention is directed to a novel dioxin compound and the use of the novel compound in creating fragrances, and scents in items such as perfumes, colognes and personal care products.

19 Claims, No Drawings

METHYLENE DIOXY OCTAHYDROINDENE DERIVATIVES

FIELD OF THE INVENTION

The present invention relates to new chemical entities and the incorporation and use of the new chemical entities as fragrance materials.

BACKGROUND OF THE INVENTION

U.S. Pat. No. 6,303,798, hereby incorporated by reference, discusses the use of substituted tetrahydroindane derivatives as useful fragrance materials. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides a novel chemical, and the use of this chemical to enhance the fragrance of perfumes, toilet waters, colognes, personal products and the like. In addition, the present invention is directed to the use of the novel chemical to enhance fragrance in perfumes, toilet waters, colognes, personal products and the like.

More specifically, the present invention is directed to the novel compound, 4a, 4b,8,8-tetramethyl-4,4a,4b,5,6,7,8,9a-octahydroindeno[2,1-d][1,3]dioxine, which is understood to be represented by the formula below:

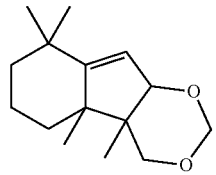

Another embodiment of the invention is a method for enhancing a perfume by incorporating an olfactory acceptable amount of the compound provided above.

These and other embodiments of the present invention will be apparent by reading the following specification.

DETAILED DESCRIPTION OF THE INVENTION

The novel compound of the present invention is prepared by the reaction of 5,6,7,7a-tetrahydro-1,4,4,7a-tetramethyl-4H-indene with paraformaldehyde. Preparation of 5,6,7,7a-tetrahydro-1,4,4,7a-tetramethyl-4H-indene is discussed in U.S. Pat. No. 3,911,027. The paraformaldehyde is preferably diluted, having a weight percent value of from about 20 to about 50, preferably of from about 30 to about 40 and most preferably about 37. A Lewis acid catalyst is preferably employed in the reaction. The preferred Lewis acid is boron trifluoride etherate complex. A preferred method of carrying out the reaction is by refluxing the components at an elevated temperature, from about 50° C. to about 120° C., preferably from about 65° C. to about 110° C. and most preferably at about 105° C.

Those with skill in the art will recognize that the compounds of the present invention have several chiral centers, thereby providing numerous isomers of the claimed compounds. As used herein the compounds described herein include the isomeric mixtures of the compounds as well as those isomers that may be separated using techniques known to those with skill in the art. Suitable techniques include chromatography, particularly gel chromatography.

The optical isomers for the compound 4a,4b,8,8-tetramethyl-4,4a,4b,5,6,7,8,9a-octahydroindeno[2,1-d][1,3]dioxine are provided in the following table. One with skill in the art would be able to formulate fragrance compositions using one or more or the following isomers and mixtures of the isomers:

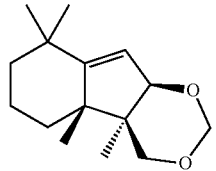

(4aR,4bR,9aR)-4a,4b,8,8-tetramethyl-4,4a,4b,5,6,7,8,9a-octahydroindeno[2,1-d][1,3]dioxine

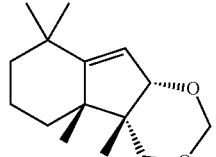

(4aS,4bR,9aS)-4a,4b,8,8-tetramethyl-4,4a,4b,5,6,7,8,9a-octahydroindeno[2,1-d][1,3]dioxine

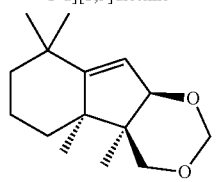

(4aR,4bS,9aR)-4a,4b,8,8-tetramethyl-4,4a,4b,5,6,7,8,9a-octahydroindeno[2,1-d][1,3]dioxine

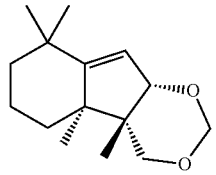

(4aS,4bS,9aS)-4a,4b,8,8-tetramethyl-4,4a,4b,5,6,7,8,9a-octahydroindeno[2,1-d][1,3]dioxine The compound of the present invention has a powerful amber note, with a sweet, warm woody character.

The use of the compound of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc.

EXAMPLE 1

Preparation of 4a,4b,8,8-tetramethyl-4,4a,4b,5,6,7,8, 9a-octahydroindeno[2,1-d][1,3]dioxine.

A mixture of 222 grams of paraformaldehyde, 32.7 grams of boron trifluoride etherate complex, and 600 mL of toluene was heated to reflux at 108° C. Then 309 grams of 5,6,7, 7a-tetrahydro-1,4,4,7a-tetramethyl-4H-indene was fed into the reaction mixture over two hours. Preparation of 5,6,7, 7a-tetrahydro-1,4,4,7a-tetramethyl-4H-indene is disclosed in U.S. Pat. No. 3,911,027. The mass was aged at reflux at 108° C. for three hours. The mixture was then cooled to 50° C. Aqueous sodium hydroxide solution (20%) 1.5 L was added to the mixture. The aqueous layer was discarded and the organic layer was washed twice with 500 milliliters of 10% sodium carbonate solution.

The organic layer was distilled to recover the toluene, as well as 290 grams of 4a,4b,8,8-tetramethyl-4,4a,4b,5,6,7,8, 9a-octahydroindeno[2,1-d][1,3]dioxine (boiling point 120-124° C. at 2 mmHg).

The nmr spectrum of the 4a,4b,8,8-tetramethyl-4,4a,4b, 5,6,7,8,9a-octahydroindeno[2,1-d][1,3]dioxine is as follows: 1.00-1.10 ppm (m, 2H), 1.05 ppm (s, 3H), 1.11 ppm (s, 3H), 1.15 ppm (s, 3H), 1.29 ppm (s, 3H), 1.36-1.40 ppm (m, 1H), 1.51-1.56 ppm (m, 2H), 1.78-1.90 ppm (m, 1H), 3.42 ppm (d, 1H), 3.79 ppm (d, 1H), 4.77 ppm (d, 1H), 4.82 ppm (d, 1H), 4.65 ppm (s, 1H), 5.50 ppm (s, 1H).

EXAMPLE 2

Incorporation of 4a,4b,8,8-tetramethyl-4,4a,4b,5,6,7, 8,9a-octahydro-indeno[2,1-d][1,3]dioxine into a fragrance formulation A fragrance was prepared according to the following formulation:

| Material | Parts |
|---|---|
| TRIPLAL ® (IFF) | 0.8 |
| Allyl cyclohexyl propionate | 0.5 |
| BORNAFIX ® (IFF) | 10.4 |
| CYCLABUTE ® (IFF) | 9.0 |
| APHERMATE ® (IFF) | 15 |
| Ethyl methyl phenyl glycidate | 1.0 |
| CYCLOGALBANIFF (IFF) | 0.5 |
| Isoamylbutyrate | 1.0 |
| ISOCYCLOCITRAL ® (IFF) | 0.5 |
| JASMAL ® (IFF) | 3.0 |
| Menthone | 0.3 |
| Peach aldehyde | 12.0 |
| 4,4a,5,6,7,8,9,9b-octahydro-7,7,8,9,9-pentamethyl-indano[4,5-d]-dioxin | 10.0 |
| Phenyl acetate | 4.0 |
| HC VERDOX ® (IFF) | 28 |
| FRUCTONE ® (IFF) | 4.0 |

The fragrance was described as having a green, musky scent from the incorporation of the compound of the present invention.

What is claimed is:

1. A compound 4a,4b,8,8-tetramethyl-4,4a,4b,5,6,7,8,9a-octahydroindeno[2,1-d][1,3]dioxine.

2. The compound of claim 1, having any of the following isomeric configurations (4aR,4bR,9aR)-4a,4b,8,8-tetramethyl-4,4a,4b,5,6,7,8,9a-octahydroindeno[2,1-d][1,3]dioxine; (4aS,4bR,9aS)-4a,4b,8,8-tetramethyl-4,4a,4b,5,6,7,8, 9a-octahydroindeno[2,1-d][1,3]dioxine; (4aR,4bS,9aR)-4a, 4b,8,8-tetramethyl-4,4a,4b,5,6,7,8,9a-octahydroindeno[2,1-d][1,3]dioxine; (4aS,4bS,9aS)-4a,4b, -tetramethyl-4,4a,4b, 5,6,7,8,9a-octahydroindeno[2,1-d][1,3]dioxine.

3. The compound of claim 1 which is incorporated into a fragrance formulation.

4. A method for improving, enhancing or modifying the odor properties of a fragrance by incorporating an olfactory acceptable amount of 4a,4b,8,8-tetramethyl-4,4a,4b,5,6,7,8, 9a-octahydroindeno[2,1-d][1,3]dioxine.

5. The method of claim 4, wherein the amount of 4a,4b, 8,8-tetramethyl-4,4a,4b,5,6,7,8,9a-octahydroindeno[2,1-d][1,3]dioxine incorporated into a fragrance is from about 0.005 to about 10 weight percent.

6. The method of claim 4, wherein the amount of 4a,4b, 8,8-tetramethyl-4,4a,4b,5,6,7,8,9a-octahydroindeno[2,1-d][1,3]dioxine incorporated into a fragrance is from about 0.5 to about 8 weight percent.

7. The method of claim 4, wherein the amount of 4a,4b, 8,8-tetramethyl-4,4a,4b,5,6,7,8,9a-octahydroindeno[2,1-d][1,3]dioxine incorporated into a fragrance is from about 1 to about 7 weight percent.

8. The method of claim 4 wherein the fragrance is incorporated into a product selected from perfumes, colognes, toilet waters, personal care products, cleaning products and air fresheners.

9. The method of claim 8 wherein the cleaning product is selected from the group consisting of detergents, dishwashing compositions, scrubbing compounds and window cleaners.

10. The method of claim 8 wherein the product is a personal care product.

11. A method for the preparation of the compound of claim 1, comprising reacting 5,6,7,7a-tetrahydro-1,4,4,7a-tetramethyl-4H-indene with a solution of paraformaldehyde.

12. A method of claim 11, wherein the weight percent value of paraformaldehyde in the solution is from about 20 to about 50.

13. A method of claim 11, wherein the weight percent value of paraformaldehyde in the solution is from about 30 to about 40.

14. A method of claim 11, wherein the weight percent value of paraformaldehyde in the solution is about 37.

15. A method of claim 11, wherein the reaction is performed in the presence of a Lewis acid catalyst.

16. A method of claim 15, wherein the Lewis acid catalyst is boron triflouride.

17. A method of claim 11, wherein the temperature of the reaction mixture is from about 50° C. to about 120° C.

18. A method of claim 11, wherein the temperature of the reaction mixture is from about 65° C. to about 110° C.

19. A method of claim 11, wherein the temperature of the reaction mixture is about 105° C.

* * * * *